United States Patent [19]

Kohl et al.

[11] Patent Number: 5,076,178
[45] Date of Patent: Dec. 31, 1991

[54] SYRINGE NEEDLE DESTRUCTION METHOD AND APPARATUS

[75] Inventors: Brad A. Kohl, Athens; Kenneth C. Musgrave, Atlanta; Randall D. Decker, Tucker, all of Ga.

[73] Assignee: Medical Safety Technologies, Inc., Bogart, Ga.

[21] Appl. No.: 653,076

[22] Filed: Feb. 11, 1991

[51] Int. Cl.⁵ .......................... F23G 5/00; F23G 5/10
[52] U.S. Cl. .................................... 110/250; 128/919; 219/68; 110/346
[58] Field of Search ..................... 110/250, 346, 237; 219/68; 128/919

[56] References Cited

U.S. PATENT DOCUMENTS

| | | |
|---|---|---|
| 4,255,996 | 3/1981 | Choksi et al. . |
| 4,445,644 | 5/1984 | Lemke . |
| 4,628,169 | 12/1986 | Ch'ing-Lung . |
| 4,860,958 | 8/1989 | Yerman . |
| 4,877,934 | 10/1989 | Spinello . |
| 4,905,916 | 3/1990 | Sorwick et al. . |
| 4,934,283 | 6/1990 | Kydd .......................... 110/250 X |
| 4,961,541 | 10/1990 | Hashimoto . |
| 4,965,426 | 10/1990 | Colombo . |
| 4,969,379 | 11/1990 | Taylor et al. . |
| 5,005,496 | 4/1991 | Nagata ........................... 110/237 X |

FOREIGN PATENT DOCUMENTS 0010126  12/1988  European Pat. Off. ............ 128/919

Primary Examiner—Edward G. Favors
Attorney, Agent, or Firm—Kennedy & Kennedy

[57] ABSTRACT

A method and apparatus are disclosed for destroying syringe needles. The apparatus has an incinerator into which a syringe needle may be inserted, crimped by a crimper 30, burned by passing an electric current through the needle between the needle tip and a sealing crimp formed by the crimper 30, and the burned needle severed by a cutter 36.

14 Claims, 5 Drawing Sheets

SYRINGE NEEDLE DESTRUCTION METHOD AND APPARATUS

TECHNICAL FIELD

This invention relates to methods and apparatuses for destroying syringe needles.

BACKGROUND OF THE INVENTION

Disposable hypodermic syringes are widely used in hospitals and other medical facilities to draw body fluids from and to inject medications into patients. These syringes are made disposable because of the difficulties and inefficiencies involved in re-sterilizing syringes for reuse. Because the syringes are intended to be disposed of after use, a problem arises as to their safe post-use storage and disposal and in preventing them from being recklessly reused by others. By law syringes may not be disposed of as ordinary waste since their sharp needle tips, as well as disease causing organisms sometimes carried by them, may injure hospital and waste disposal personnel.

To dispose of syringes safely, devices have been devised that mechanically sever the syringe needles from their barrels. These are exemplified by those shown in U.S. Pat. Nos. 4,255,996, 4,445,644 and 4,969,379. Though these devices do prevent reuse of syringes, a sharp needle stub remains intact and hazardous. Other types of syringe destruction devices grind the syringes into small pieces as shown in U.S. Pat. No. 4,905,916. These however do not provide for sanitary syringe residue disposal. Furthermore, their shearing action tends to release fluid contaminates to ambience.

Incinerators have also been used to destroy syringes is a sanitary manner. Bulk incineration of accumulated syringes however poses the threat of injury still occurring during accumulation and incineration input. Thus, portable devices have been used which can incinerate the needles by passing an electric current through them. This approach is described in U.S. Pat. No. 4,877,934 and 4,965,426. These devices however leave the barrel portion of the syringe with an opening at one end through which contaminates may emerge to ambience. Furthermore, some pathogens contained within the needle and expelled from the syringe during insertion are not killed by the incineration process.

It thus is seen that a need remains for a method and apparatus for destroying syringe needles in a more effective and efficient manner. It is to the provision of such that the present invention is primarily directed.

SUMMARY OF THE INVENTION

In a preferred form of the invention, a syringe needle destruction apparatus comprises a housing having an orifice through which a syringe needle may be inserted into the housing. Crimping means are mounted within the housing adjacent the orifice for crimping a syringe needle to substantially seal the syringe. A needle tip contact element is mounted for movement along a needle path of travel within the housing in engagement with the needle tip. The apparatus also has means for establishing a voltage across the crimping means and the needle tip contact element sufficient to burn that portion of the needle that extends between the needle crimp and tip.

In another preferred form of the invention, a method provides for destroying a portion of a hollow needle that extends outwardly from the barrel and hub of a syringe to a needle tip. The method comprises the steps of inserting the needle portion into an incinerator while leaving the barrel outside of the incinerator, forming a sealing crimp in the hollow needle, and burning the needle by passing an electric current through the needle between the needle crimp and tip.

DETAILED DESCRIPTION

Figure 1:
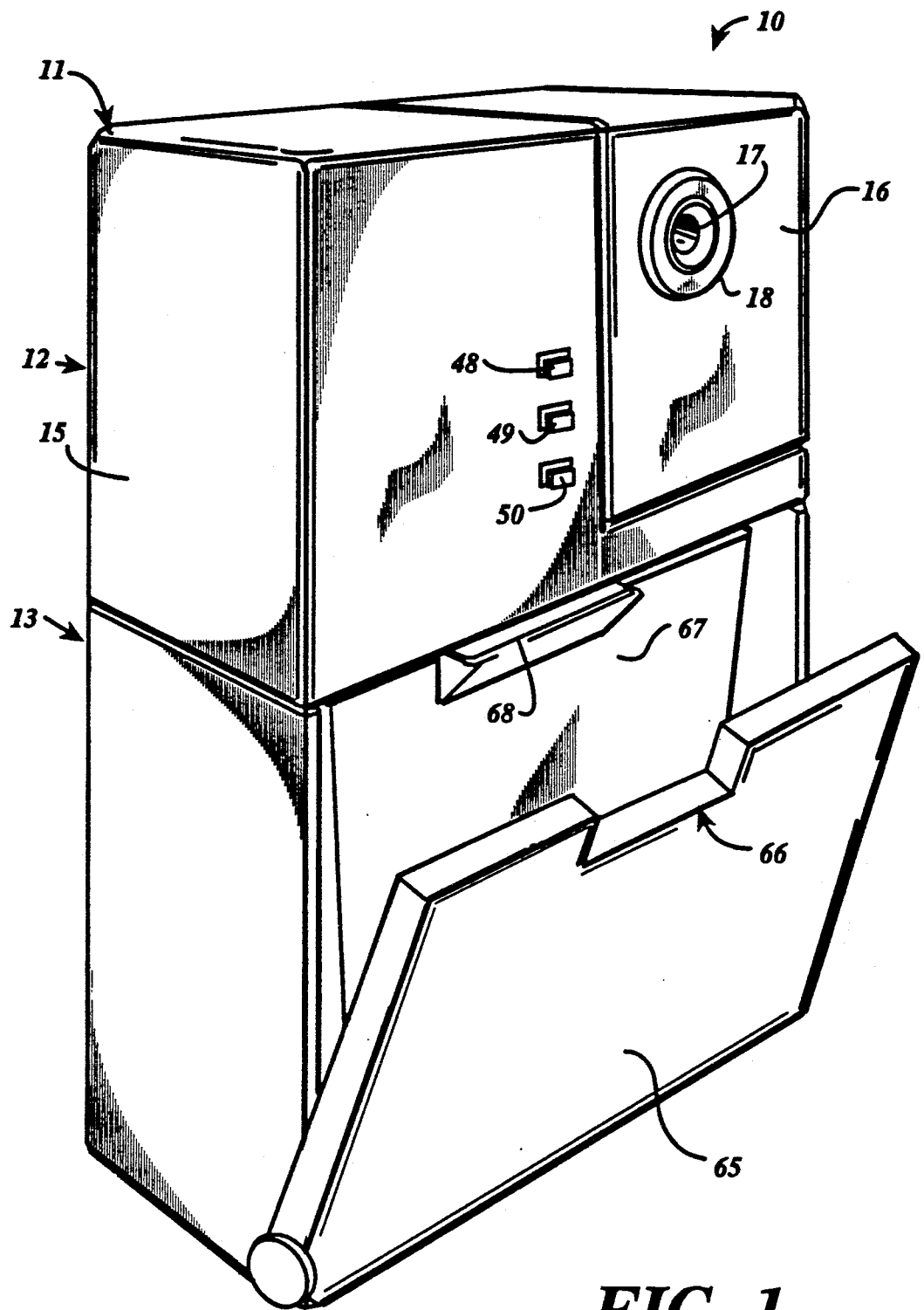
FIG. 1 is a perspective view of a syringe needle destruction apparatus that embodies principles of the invention is a preferred form.
Figure 2:
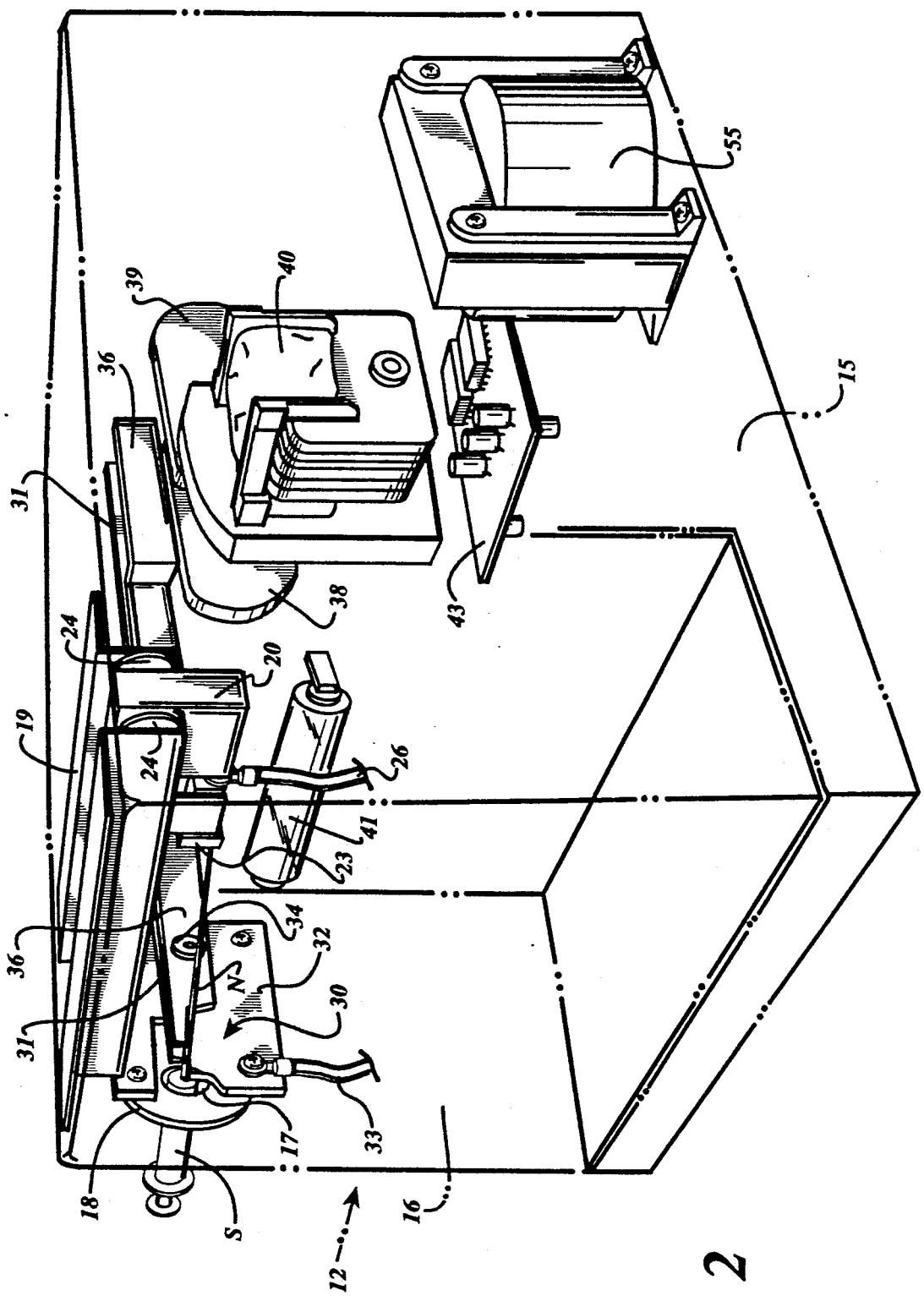
FIG. 2 is a perspective view of internal components of the apparatus of FIG. shown with the housing and a portion of the electric wiring removed for clarity.

With reference next to the drawings, there is shown an apparatus 10 having a housing 11 The housing 11 has an upper, self-contained unit 12 for syringe needle destruction operations that is mounted atop a lower, self-contained unit 13 in which residual syringe barrels may be collected and stored. The upper unit is shown in FIG. 2 as having a main power supply housing 15 to which an incinerator housing 16 is removably mounted. The incinerator housing 16 has a conically shaped needle receiving orifice guide 17 mounted about a central orifice. An annular activation switch, shown generally at 18, is mounted about the orifice guide 17 to the front of the housing 16. The activation switch 18 is coupled by means of conductors 21 with a controller 22 mounted within the housing 15.

A track 19 is mounted within the housing above the orifice guide 17. A spring biased carriage 20 is movably supported for travel upon the track 19. The carriage 20 bears an electrode 23 with a concave face that faces and is aligned with the needle orifice. The carriage 20 has four wheels 24 rollably positioned upon the track 19, and a coil spring 25 having one end mounted to the track so as to bias the carriage towards the needle orifice. A flexible conductor 26 connects the carriage electrode 23 to a transformer 55 in all positions of the carriage along the track.

A needle crimping means 30 is mounted in housing 16 closely adjacent to the needle orifice. The crimping means comprises an upper crimping plate 31 pivotably mounted on a pivot pin 34 above the orifice and a stationary lower crimping plate 32 rigidly mounted below the needle orifice. The lower plate 32 also functions as an electrode. A conductor 33 couples the lower plate 32 with the transformer 55.

Figure 3:
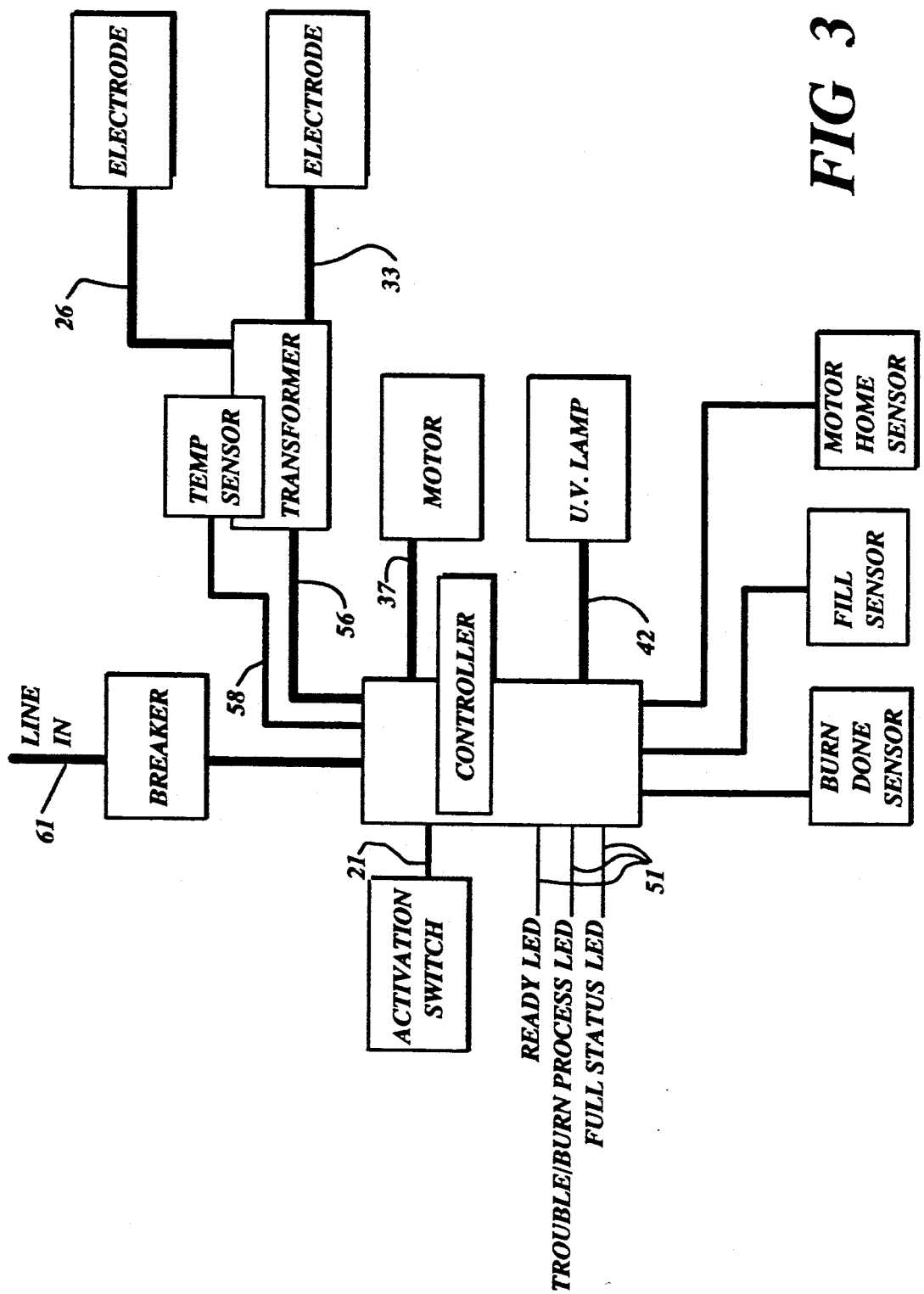
FIG. 3 is a block diagram of the apparatus of FIG. 1.
Figure 4:
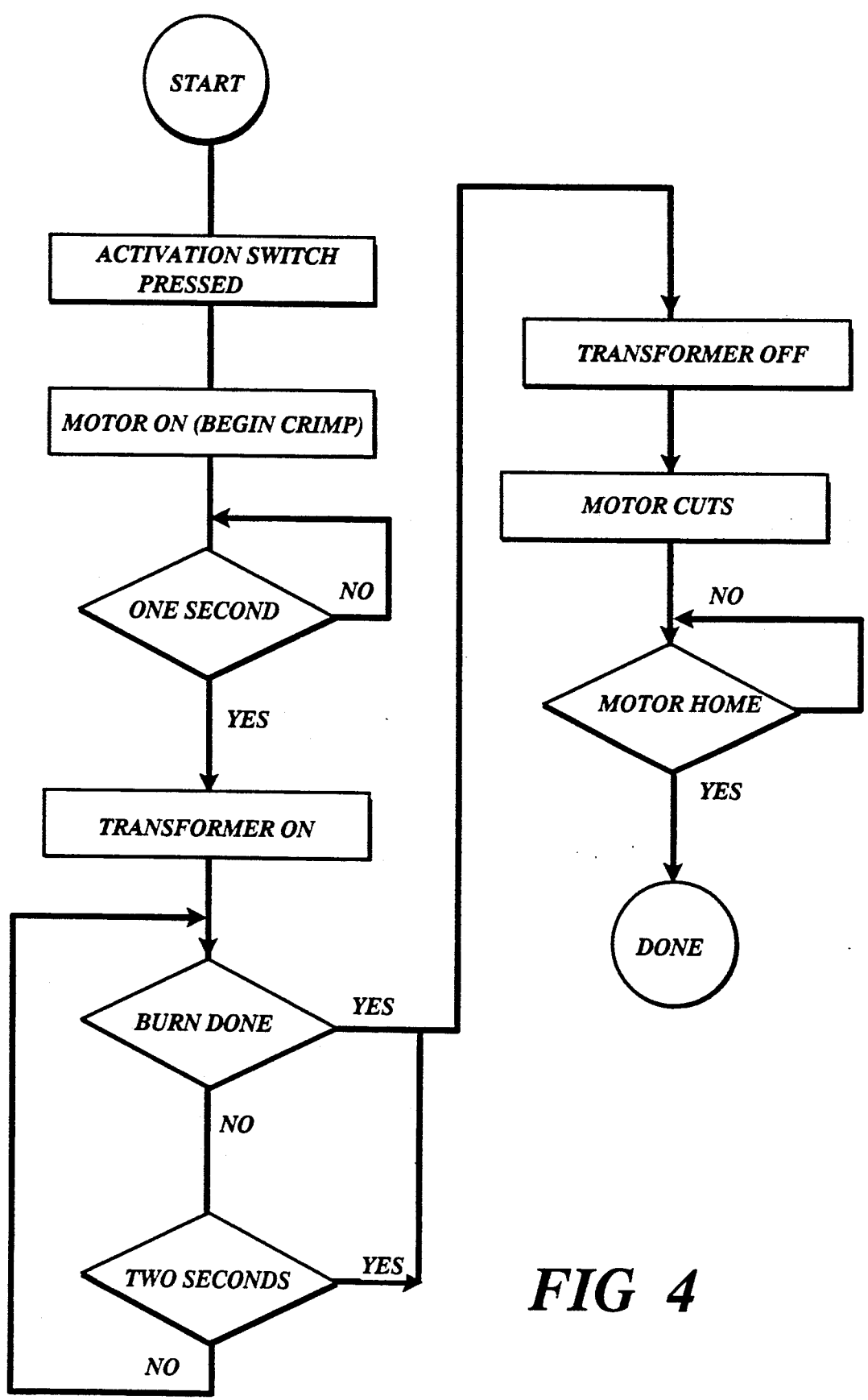
FIG. 4 is a flow diagram of the operation of the apparatus of FIG. 1 and method of the invention.

The apparatus also has means for severing needles that includes a pivotable cutting blade or shearing plate 36 pivotable mounted on a pivot pin 34 in sliding contact with the rear side of the upper crimping plate 31. Both the upper crimping plate 31 and the blade 36 extend through aligned openings in two adjacent walls of the housing units 15 and 16 so that one of their end portions is within the confines of the main power supply housing 15. An electric motor 40, mounted in the main power supply housing 15, has its power output drive shaft coupled with both a crimping cam 38 and a cutting cam 39. The motor is electrically coupled to the controller 22 by means of control line 37, as shown in FIG. 3. An ultraviolet light 41, mounted in the incinerator housing 16, is also coupled with the controller by a conductor 42. A system ready LED type indicator lamp 48, a trouble/burn process LED type indicator lamp 49, and a full status LED type indicator lamp 50 are all mounted to the front of the incinerator housing 15. Each is connected to the controller 22 via a line or cable 51 of ganged conductors.

As shown best in FIG. 3, transformer 55 is coupled to the controller 22 by a conductor 56. A high temperature sensor is mounted on the transformer 55 coupled with the controller by conductor 58. The carriage electrode 23 and the lower crimping plate/electrode 32 are coupled with the transformer by means of conductors 26 and 33, respectively.

A photoelectric burn done sensor is also mounted within the incinerator unit 16. This sensor is mounted so that the carriage 20 interrupts its beam when the carriage is at a position closely adjacent the orifice. An unshown motor home sensor is mounted adjacent the motor 40 to indicate that the cams have completed a full cycle so as to have returned to their initial, apparatus-ready positions prior to apparatus activation.

Finally, the housing lower portion 13 has a door 65 that is provided with a slot 66 located on its top edge. A removable bin 67 is located within the housing lower portion 13 which has a contoured chute 68 sized to extend through the door slot 66 when the door is closed.

OPERATION

Figure 5A:
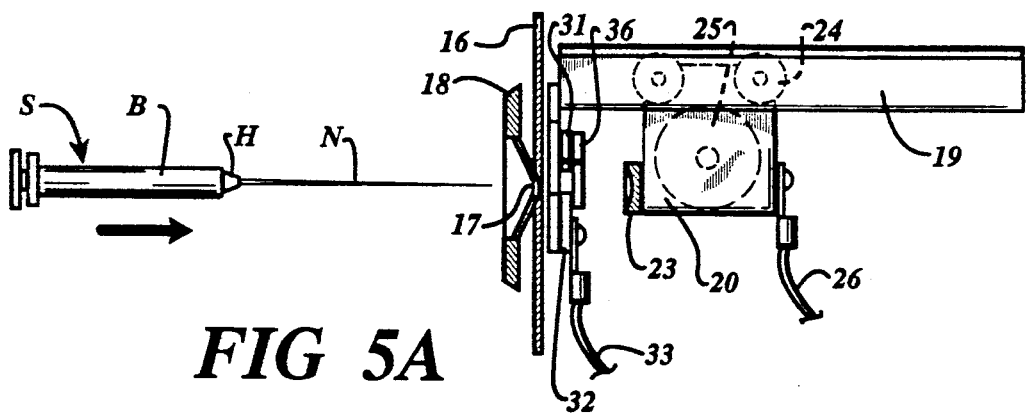
FIGS. 5A–5F are a sequence of views, shown in crosssection, of a portion of the apparatus of FIG. 1, showing a syringe needle being inserted, crimped, incinerated and severed in accordance with a method of the invention.
Figure 5B:
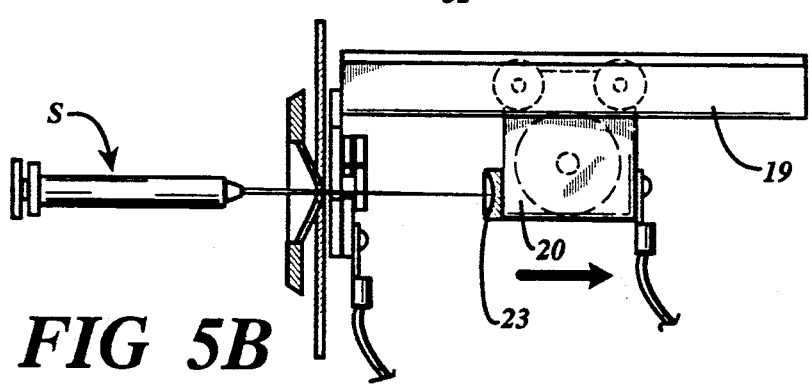
Figure 5C:
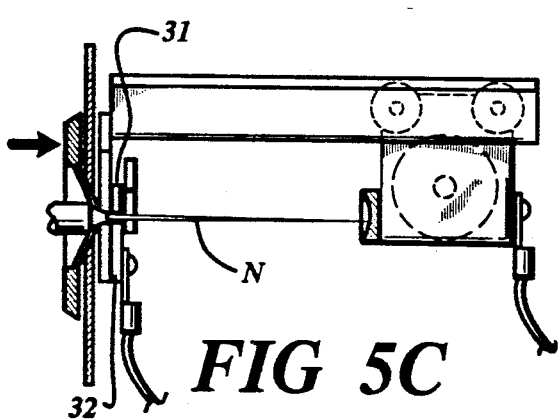

Operation of the apparatus may best by understood by reference to FIGS. 5A-5F. In FIG. 5A a conventional syringe S having a barrel B, a plastic needle hub H, and a metallic, needle N is guided by an operator, such as a nurse, nurse's aid, or hospital attendant, into the needle receiving orifice. The conical shape of the orifice guide 17 serves to guide the needle tip into and through the orifice. As the needle N is pushed into the incinerator housing 16 it passes between the crimping plates 31 and 32 bringing its tip into contact with the carriage electrode 23. As the needle is pushed further into the unit it drives the carriage 20 away from orifice along track 19, against the bias provided by spring 25, as shown in FIG. 5B, until either the syringe hub H abuts the conical orifice guide, as shown in FIG. 5C, or until the carriage has traveled the maximum distance allowed by the track 19 by engaging an unshown carriage stop. Carriage movement is limited to insure that an operator does not attempt to incinerate the entire length of an extraordinarily long needle in a single operations and thereby exceed power capacity limits. Such long needles are instead incinerated in a succession of operations as such operations are herein described.

Once the syringe is fully inserted into the incinerator, as shown in FIG. 5C, the operator depresses the activation switch 18 as with his or her finger while holding the syringe barrel. In response to this the controller 22, which is of conventional construction that preferably employs a microprocessor chip, energizes the motor 40 and the trouble/burn process lamp 49, and deenergizes the system ready lamp 48. The motor then commences to rotate the crimping cam 38 and the cutting cam 39. The crimping cam 38 engages and pivots the upper crimping plate 31 about pivot pin 34 thereby crimping needle N between the upper crimping plate 31 and the lower crimping plate 32, as shown in FIG. 5C. The crimping of the needle serves the dual function of sealing the syringe needle residual stub and providing an electric contact with the needle at the crimp site since the lower plate 32 also functions as an electrode.

With the needle crimp still held firmly by the plates 31 and 32, the controller next energizes the electrodes 23 and 32 by coupling them with the transformer 55 and its 7 volt A.C. voltage. For the electrical resistance provided by a 16 gauge stainless steel needle portion of a length approximately three an one half inches between the electrodes 23 and 32, approximately 40 amps is caused to flow through it causing the needle portion to burn and char throughout in less than a second. This general voltage level is preferred as substantially higher voltage levels can cause sparking and welding of the needle to the electrodes and substantially lower voltages can lead to insufficient or too slow incineration.

Figure 5D:
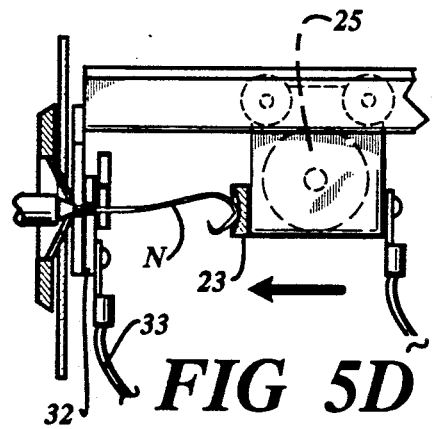

During the brief period of incineration, the spring 25 continuously urges the two electrodes towards one another. This serves to maintain them in good contact with the needle and also to create a compaction force on the needle char to lengthen the time that the charring needle provides a conductive path between the electrodes. As incineration progresses and the needle weakens, it becomes unable to hold the electrodes apart. As a result, the carriage and electrode 23 then advance towards the crimping means, as shown in FIG. 5D. This causes the needle to fold and twist which usually forms it into a compact, single extension needle residue char of a coil-like shape that usually remains attached to the unburned portion of the needle at its crimp.

Figure 5E:
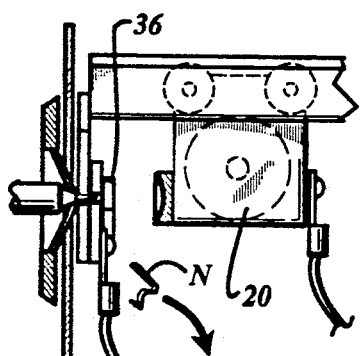
Figure 5F:
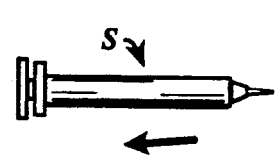
Figure 5F:
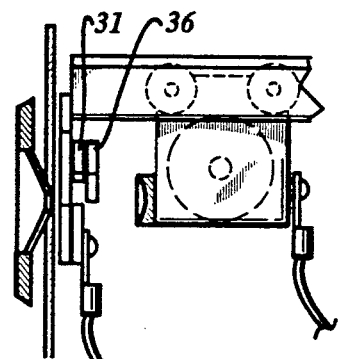

Upon return of the carriage to its initial position adjacent the crimping means 30, the carriage interrupts the photoelectric burn done sensor beam which indicates to the controller that the burn process is complete. The controller then de-energizes the electrodes. If the burn done sensor beam has not been interrupted after expiration of a two second time period from burn initiation, the controller de-energizing the electrodes anyway. It is at approximately this time that the cutting cam 39 has rotated to a position forcing the cutting blade 36 downward through the needle char closely adjacent the crimp. The cutting blade severs the residue char whereupon it free falls, as shown in FIG. 5E, to the bottom of the incinerator. With the crimping plates once again separated, the needle crimp is released enabling the operator to remove the syringe and its short, sealed, needle stub from the incinerator unit and place it in the lower storage unit. Once the cams have fully returned to their initial positions a motor home or cycle complete sensor inputs a signal to the controller 22 which de-energizes the motor 40, re-energizes the system ready lamp 48, and de-energizes the trouble/burn process 49 to indicate that the apparatus is reset and ready to incinerate another needle.

Though most pathogens within the needle are killed by its incineration, some heat resistant ones may not be. Also, some pathogens may be expelled during insertion and operation of the needle into the apparatus. For these reasons the incinerator is also provided with a germicidal ultraviolet light 41 which is energized by the controller for a short time following needle severance to kill such remaining pathogens. Once the fill sensor lamp indicates that the incinerator housing 16 is filled to capacity, it may by removed for disposal. Alternatively, the incinerator housing may have a disposable collecting bin removably mounted within the incinerating housing 16.

From the foregoing, it is seen that a method and apparatus for destroying syringe needles is now provided which overcomes problems associated with those of the prior art. It should however be understood that the just described embodiment merely illustrates principles of the invention in a preferred form. Many modifications, additions and deletions may, of course, be made thereto without departure from the spirit and scope of the invention as set forth in the following claims.

We claim:

1. A syringe needle destruction apparatus comprising a housing having an orifice through which a syringe needle may be inserted into the housing, crimping means mounted within said housing adjacent said orifice for crimping a syringe needle to substantially seal the syringe, a needle tip contact element mounted for movement along a needle path of travel within said housing in engagement with the needle tip, and means for establishing a voltage across said crimping means and said needle tip contact element sufficient to burn that portion of the needle that extends between the needle crimp and tip.

2. The syringe needle destruction apparatus of claim 1 wherein said needle tip contact element is mounted for movement by mounting means that comprises a track mounted within said housing extending substantially parallel to the needle path of travel, and a carriage movably mounted upon said track and spring biased towards said orifice to which carriage said needle tip contact element is mounted.

3. The syringe needle destruction apparatus of claim 1 wherein said crimping means comprises a pair of plates and motor means coupled to at least one of said plates for imparting relative movement of the crimping plates towards each other.

4. The syringe needle destruction apparatus of claim 1 further comprising cutting means mounted within said housing adjacent said crimping means for severing a burned portion of the needle from a substantially unburned portion.

5. The syringe needle destruction apparatus of claim 4 wherein said cutting means comprises a shearing plate mounted in sliding contact with said crimper means.

6. The syringe needle destruction apparatus of claim 1 further comprising a germicidal ultraviolet light generating means mounted within said housing.

7. A method of destroying at least a portion of a needle needle that extends outwardly from the barrel and hub of a syringe to a needle tip, and with the method comprising the steps of:

(a) inserting the needle portion into an incinerator while leaving the barrel outside of the incinerator;

(b) forming a sealing crimp in the hollow needle adjacent the syringe hub;

(c) burning the needle by passing an electric current through the needle between the needle crimp and tip.

8. The method of claim 7 further comprising the steps of:

(d) severing the burned portion of the needle adjacent the crimp.

9. The method of claim 8 wherein the crimping, burning and severing steps are preformed in sequence.

10. The method of claim 8 wherein the needle is irradiated with ultraviolet light within the incinerator housing.

11. A syringe needle destruction apparatus comprising;

means for receiving and containing an exposed needle portion of a syringe;

means for forming a crimp in the needle distally from the needle tip; and means for passing an electric current through said exposed needle portion.

12. The syringe needle destruction apparatus of claim 11 further comprising means for severing the exposed needle portion adjacent the crimp.

13. The syringe needle destruction apparatus of claim 12 further comprising control means for controlling said needle crimping means, said electric current passage means and said needle severing means in a sequence of operations.

14. A syringe needle destruction apparatus comprising a main housing and an incinerator housing detachably mounted to said main housing, said incinerator housing having an orifice, a track mounted in said incinerator housing, a carriage movable mounted on said track and spring biased toward said orifice, crimping means mounted within said incinerator housing for forming a crimp in a syringe needle inserted into said incinerator housing through said orifice, means for establishing a voltage across at least a portion of a syringe needle within said incinerator housing which includes an electrode mounted on said carriage facing said orifice, and severing means mounted in said incinerator housing for severing at least a portion of a needle inserted into said incinerator housing between a crimp formed in the needle by said crimping means and the needle tip.

* * * * *